United States Patent [19]

Yamanaka et al.

[11] Patent Number: 4,533,669

[45] Date of Patent: Aug. 6, 1985

[54] ANTI-DEPRESSANT IMIDAZOLES

[75] Inventors: Motosuke Yamanaka, Abiko; Isao Saito, Chofu; Kiyomi Yamatsu, Kamakura; Takako Fujimoto, Yokohama, all of Japan

[73] Assignee: Eisai Co., Ltd., Tokyo, Japan

[21] Appl. No.: 469,548

[22] Filed: Feb. 25, 1983

Related U.S. Application Data

[62] Division of Ser. No. 252,674, Apr. 9, 1981, Pat. No. 4,402,966, which is a division of Ser. No. 93,469, Nov. 13, 1979, Pat. No. 4,301,169.

[30] Foreign Application Priority Data

Nov. 14, 1978 [JP] Japan .................................. 53-139325
Nov. 21, 1978 [JP] Japan .................................. 53-142813

[51] Int. Cl.³ .................. A61K 31/415; C07D 233/61; C07D 233/56
[52] U.S. Cl. ..................................... 514/396; 514/399; 548/236; 548/342; 548/346
[58] Field of Search ...................... 548/346; 424/273 R

[56] References Cited

U.S. PATENT DOCUMENTS

| | | | |
|---|---|---|---|
| 3,637,731 | 1/1972 | Johnson | 548/346 |
| 4,172,947 | 10/1979 | Warner et al. | 548/346 |
| 4,284,641 | 8/1981 | Thorogood | 424/273 R |
| 4,431,815 | 2/1984 | Thorogood | 548/346 X |

FOREIGN PATENT DOCUMENTS 1578644 8/1969 France .................................. 548/346

OTHER PUBLICATIONS

Chemical Abstracts, 72: 1215293z (1970), [France 1,578,644, 8/14/69].

Primary Examiner—Richard A. Schwartz
Attorney, Agent, or Firm—Flynn, Thiel, Boutell & Tanis

[57] ABSTRACT

An anti-depressant imidazole compound of the formula:

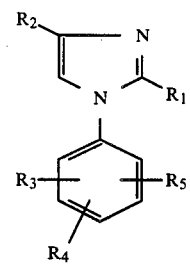

wherein $R_1$ is lower alkyl, $R_2$ is hydrogen or lower alkyl, and $R_3$, $R_4$ and $R_5$ are hydrogen, lower alkyl, trifluoromethyl, amino, mono- or di-lower alkylamino, heterocyclic amino, halogen or

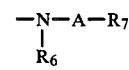

(in which $R_6$ is hydrogen, lower alkyl or lower alkylsulfonyl, A is carbonyl or sulfonyl, and $R_7$ is lower alkyl, halogenated lower alkyl, mono- or di-lower alkylamino, mono- or di- lower alkylaminoalkyl, unsubstituted phenyl or phenyl having halogen, lower alkyl, lower alkoxy or trifluoromethyl, phenylamino or phenylamino having halogen, lower alkyl, lower alkoxy or trifluoromethyl); and their pharmaceutically acceptable acid addition salts. These compounds are useful as agents for treating depression and depressive states.

19 Claims, No Drawings

ANTI-DEPRESSANT IMIDAZOLES

This application is a division of Ser. No. 252,674, filed Apr. 9, 1981, now U.S. Pat. No. 4,402,966, which in turn is a division of Ser. No. 93,469, filed Nov. 13, 1979, now U.S. Pat. No. 4,301,169.

This invention relates to novel imidazole derivatives showing excellent medical efficacy, preparation thereof and drugs containing such derivatives. More particularly, it relates to imidazole derivatives expressed by the following general formula (I), and their pharmaceutically acceptable acid addition salts,

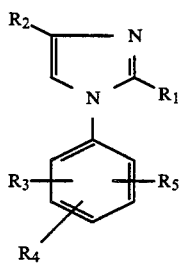

in which $R_1$ represents a lower alkyl group, $R_2$ represents a hydrogen atom or a lower alkyl group, and $R_3$, $R_4$ and $R_5$ may be the same or different and independently represent a hydrogen atom, a lower alkyl group, a trifluoromethyl group, an amino group, a mono- or di-lower alkylamino group, a heterocyclic amino group, a halogen atom or a radical of the formula,

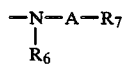

(in which $R_6$ represents a hydrogen atom, a lower alkyl group or a lower alkylsulfonyl group, A represents a carbonyl group or a sulfonyl group, and $R_7$ represents a lower alkyl group, a halogenated lower alkyl group, a mono- or di-lower alkylamino group, a mono- or di-lower alkylaminoalkyl group, an unsubstituted phenyl group or a phenyl group substituted with a halogen atom, a lower alkyl group, a lower alkoxy group or a trifluoromethyl group, an unsubstituted phenylamino group or a phenylamino group substituted with a halogen atom, a lower alkyl group, a lower alkoxy group or a trifluoromethyl group), with the proviso that there is no case where (i) $R_1$ is a methyl group, and $R_2$, $R_3$, $R_4$ and $R_5$ are hydrogen atom; or (ii) $R_1$ is a methyl group, $R_3$ is an ortho-amino group, and $R_2$, $R_4$ and $R_5$ are hydrogen atom and to a process for producing the same and also to an antidepressant containing such derivatives and addition products.

In the above general formula (I), "lower alkyl" of the lower alkyl group, lower alkoxy group, mono- or di-lower alkylamino group, halogenated lower alkyl group and mono- or di-lower alkylaminoalkyl group as appearing in the definitions of $R_1$, $R_2$, $R_3$, $R_4$, $R_5$, $R_6$ and $R_7$ is intended to mean a linear or branched alkyl group, e.g. methyl, ethyl, n-propyl, isopropyl, isobutyl, 1-methylpropyl, tert-butyl, n-pentyl, 1-ethylpropyl, isoamyl, n-hexyl or the like.

Further, the term "heterocyclic amino group" means, for example, a 1-piperidyl group, a 1-pyrrolidyl group, 4-morpholinyl group and the like.

The compounds of the formula (I) according to the invention can be readily converted into their acid addition salts by reaction with pharmaceutically acceptable inorganic or organic acids. Examples of such acid addition salt include mineral acid salts such as hydrochloride, sulfate, nitrate and the like, and organic acid salts such as oxalate, fumarate, maleate, malonate, methanesulfonate and the like.

Typical examples of the compounds according to the invention are those mentioned hereinbelow, which should not be construed as limiting the present invention thereto.

1-(3,4-Dimethylphenyl)-2-methylimidazole,
1-(3,4-Dichlorophenyl)-2-methylimidazole,
1-(3,4-Dichlorophenyl)-2-ethylimidazole,
1-(4-Aminophenyl)-2-methylimidazole,
1-(4-Aminophenyl)-2-ethylimidazole,
1-(3-Amino-4-methylphenyl)-2-methylimidazole,
1-(4-n-Butylaminophenyl)-2-methylimidazole,
1-(3,4,5-Trimethoxyphenyl)-2-methylimidazole,
1-(4-Aminophenyl)-2,4-dimethylimidazole,
1-(4-Methoxyphenyl)-2-methylimidazole,
1-(3,4-Dimethoxyphenyl)-2-methylimidazole,
1-(2-Methoxyphenyl)-2-methylimidazole,
1-(4-Fluorophenyl)-2-methylimidazole,
1-[4-(1-Piperidinylphenyl)]-2-methylimidazole,
1-(4-Dimethylaminophenyl)-2-methylimidazole,
1-(4-Chlorophenyl)-2-methylimidazole,
1-(4-Methylphenyl)-2-methylimidazole,
1-(3,4-Dimethylphenyl)-2-ethylimidazole,
1-(3,4-Dimethylphenyl)-2-n-propylimidazole,
1-(3-Trifluoromethyl-4-aminophenyl)-2-methylimidazole,
1-(2-Amino-4-trifluoromethylphenyl)-2-methylimidazole,
1-(4-Aminophenyl)-2-isopropylimidazole,
1-(2-Chloro-4-aminophenyl)-2-methylimidazole,
1-(3-Aminophenyl)-2-methylimidazole,
1-(4-Aminophenyl)-2-n-propylimidazole,
1-[4-(1-Pyrrolidinylphenyl)]-2-methylimidazole,
1-[4-(1-Morpholinophenyl)]-2-methylimidazole,
1-(4-Methylaminophenyl)-2-ethylimidazole,
1-[4-(4-Chlorobenzoylamino)phenyl]-2-ethylimidazole,
1-[2-(Dimethanesulfonylamino)phenyl]-2-methylimidazole,
1-[4-(N'-Methylureido)phenyl]-2-ethylimidazole,
1-(4-Methylsulfonylaminophenyl)-2-methylimidazole,
1-[4-(4-Methylbenzoylamino)phenyl]-2-ethylimidazole,
1-[4-(4-Chlorophenylsulfonylamino)phenyl]-2-ethylimidazole,
1-{4-[N'-(4-Chlorophenyl)ureido]phenyl}-2-methylimidazole,
1-[4-(4-Chlorobenzoylamino)phenyl]-2-methylimidazole,
1-{2-[(4-Chlorobenzoylamino)-4-trifluoromethyl]phenyl}-2-methylimidazole,
1-[4-(4-Chlorobenzoylamino)phenyl]-2,4-dimethylimidazole,
1-[4-(4-Fluorobenzoylamino)phenyl]-2-methylimidazole,
1-[4-(3,4-Dichlorobenzoylamino)phenyl]-2-ethylimidazole,
1-[4-(4-Fluorobenzoylamino)phenyl]-2-ethylimidazole,
1-[2-(4-Chlorobenzoylamino)phenyl]-2-methylimidazole,
1-[4-(4-Chlorobenzoylamino)phenyl]-2-isopropylimidazole, 1-[4-(4-Methoxybenzoylamino)phenyl]-2-ethylimidazole,
1-[4-(4-Methylbenzoylamino)phenyl]-2-methylimidazole,
1-[4-(4-Chlorobenzoylamino)phenyl]-2-n-propylimidazole,
1-[4-(4-Chlorobenzoylmethylamino)phenyl]-2-methylimidazole,
1-(4-Acetylaminophenyl)-2-methylimidazole,
1-[4-(3-Trifluorobenzoylamino)phenyl]-2-ethylimidazole,
1-(3-Aminophenyl)-2-ethylimidazole,
1-(3-Amino-4-methoxyphenyl)-2-methylimidazole,
1-(3-Dimethylaminophenyl)-2-methylimidazole,
1-(3-Methylaminophenyl)-2-methylimidazole,
1-(4-Propionylaminophenyl)2-ethylimidazole,
1-(4-Acetylaminophenyl)-2-methylimidazole,
1-(3-Propionylaminophenyl)-2-methylimidazole,
1-(3-Acetylamino-4-methoxyphenyl)-2-methylimidazole,
1-[3-(4-Chlorobenzoylamino)phenyl]-2-methylimidazole,
1-[3-(4-Chlorobenzoylamino)-4-methylphenyl]-2-methylimidazole.

The imidazole derivatives according to the invention are hitherto unknown novel compounds which show only very low toxicity and excellent antidepressant efficacy and are thus useful as a remedy or prophylactic for the depression or depressive state. As an antidepressant, there have been clinically employed compounds of a tricyclic structure such as Imipramine, Amitriptyline and the like. The compounds of the present invention are completely different in structure from those compounds.

It is accordingly an object of the present invention to provide novel imidazole derivatives which are very useful as an antidepressant and are high in safety.

It is another object of the invention to provide a process for producing novel imidazole derivatives of the above-mentioned type.

It is a further object of the invention to provide an antidepressant which comprises novel imidazole derivatives.

The compounds of the formula (I) according to the invention can be prepared by a variety of methods, typical of which are those particularly shown hereinafter.

(1) PROCEDURE A

Compounds of the formula (I) wherein $R_3$, $R_4$ and $R_5$ are not amino group and $R_2$ is a hydrogen atom can be prepared by the following method.

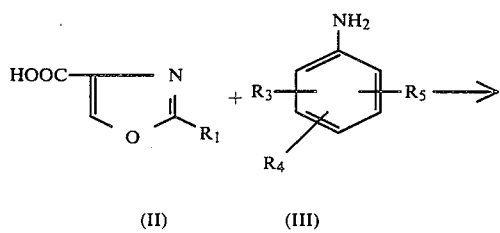

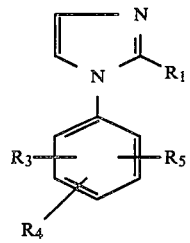

(I)

(in which $R_1$, $R_3$, $R_4$ and $R_5$ have the same meaning as defined above).

That is, the oxazole-4-carboxylic acid represented by the general formula (II) is reacted with the aniline compound represented by the general formula (III) at the temperature of approximately 160° C.–200° C. to give the intended compound of formula (I).

(2) PROCEDURE B

Compounds of the formula (I) wherein at least one of $R_3$, $R_4$ and $R_5$ is an amino group can be prepared as follows.

For instance, a nitro group-substituted phenylimidazole compound of the general formula (IV) used as a starting material

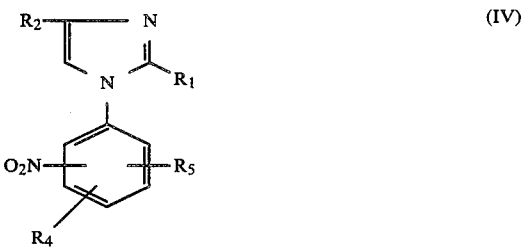

(in which $R_1$, $R_2$, $R_4$ and $R_5$ have the same meanings as defined hereinbefore) is subjected to a catalytic reduction treatment using a palladium-carbon or Raney nickel catalyst or is chemically reduced with use of iron, metallic zinc or stannous chloride to give the compound of the formula (I)

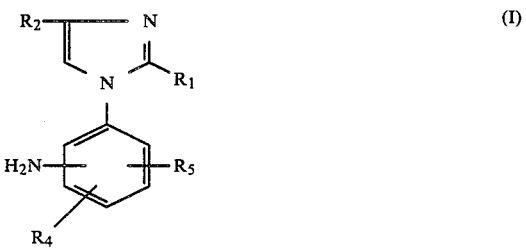

In the case $R_4$ or $R_5$ is an amino group, the same procedure is applied to.

(3) PROCEDURE C

Compounds of the general formula (I) wherein $R_1$ is a methyl group can be prepared by the following method.

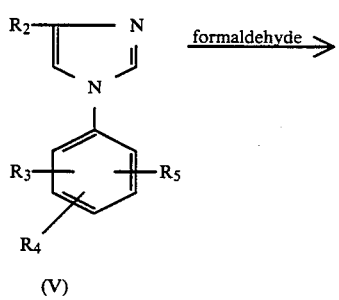

(V)

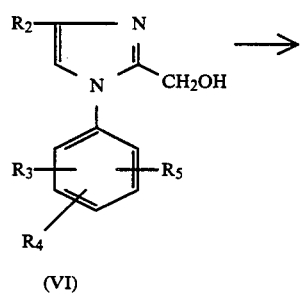

(VI)

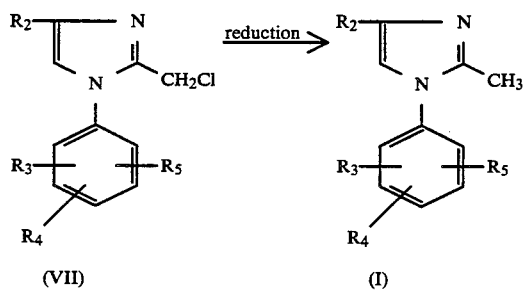

(VII)  (I)

That is, the 2-unsubstituted imidazole compound represented by the formula (V) is reacted with formaldehyde in a sealed tube to give the 2-hydroxymethyl compound represented by the formula (VI), which is then reacted, for example, with thionyl chloride to form the 2-chloromethyl compound represented by the general formula (VII), followed by catalytic reduction to give the compound of the formula (I). If compounds of the general formula (I) wherein one, or more of $R_3$, $R_4$ and $R_5$ is an amino group are desired to be obtained, a nitro-substituted compound is used as a starting material as in the case of procedure B, by which the nitro groups are reduced in the final reduction step of the above reaction to give an amino-substituted product.

(4) PROCEDURE D

Compound of the formula (I) wherein one of $R_3$, $R_4$ and $R_5$ is a mono-loweralkylamino group can be prepared by the following method.

An amino group-substituted phenylimidazole compound expressed by the general formula (VIII)

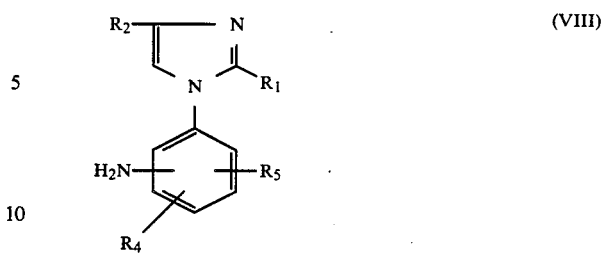

(wherein $R_1$, $R_2$, $R_4$ and $R_5$ have the same meanings as defined hereinbefore) is reacted with acetic anhydride, acetyl chloride or trifluoroacetic anhydride to produce an intermediate of the general formula (IX)

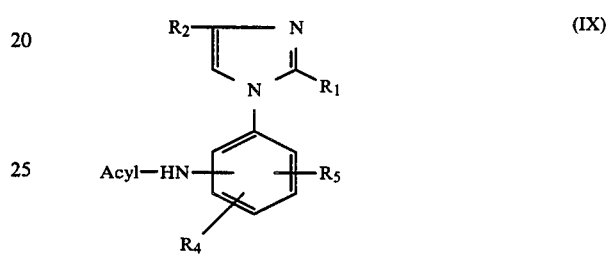

(in which Acyl represents a residue of an acetic acid or trifluoroacetic acid) and then further reacted with a lower alkyl halide to give an N,N-di-substituted amino compound represented by the general formula (X)

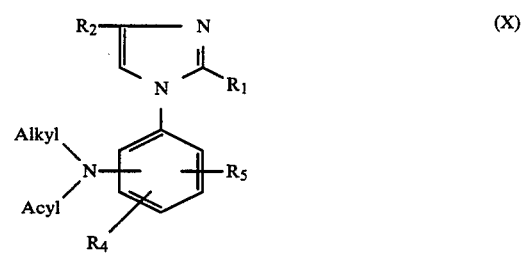

(in which Alkyl represents a lower alkyl group). The N,N-di-substituted amino compound is then hydrolyzed by means of a mineral acid or alkali to give an intended compound of the general formula (I)

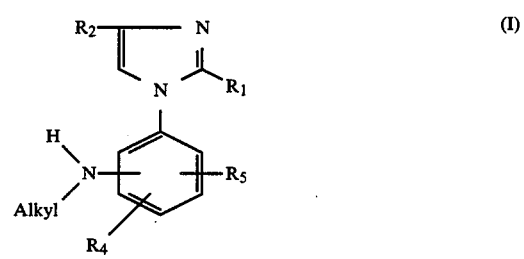

(5) PROCEDURE E

Compounds of the formula (I) wherein any of $R_3$, $R_4$ and $R_5$ are not halogen atoms can be prepared by the following method.

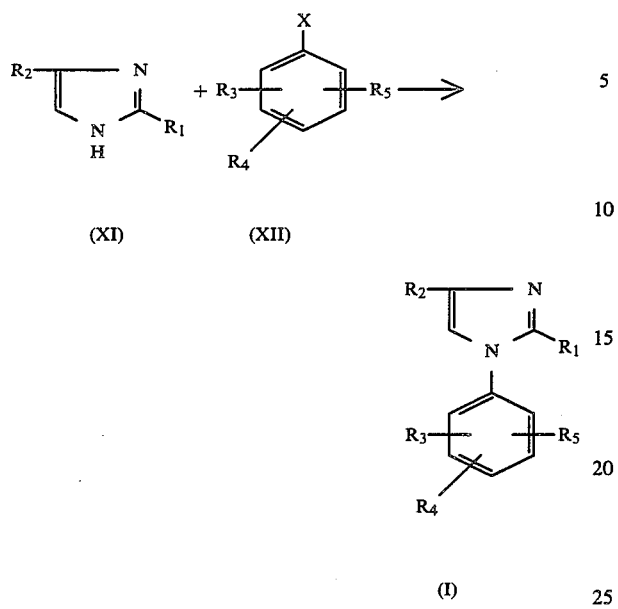

(in which X represents a halogen atom and $R_1$, $R_2$, $R_3$, $R_4$ and $R_5$ have the same meanings as defined hereinbefore, respectively)

That is, the compound expressed by the general formula (XI) and the compound expressed by the general formula (XII) are reacted in the presence of copper powder, cupric oxide, cuprous halide, γ-collidine, alkali bicarbonate, alkali carbonate, pyridine or the like under heating to obtain the compound of the formula (I). They may be used singly or in combination of two or more. The heating temperature varies depending on the reaction conditions but is preferably in the range of about 190°–210° C. In the above formula, X represents a halogen atom as mentioned and is preferably bromine or chlorine.

(6) PROCEDURE F

Compounds of the formula (I) wherein one of $R_3$, $R_4$ and $R_5$ is a group represented by the formula,

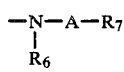

(in which $R_6$ and $R_7$ have the same meanings as defined above, respectively) can be prepared by the following methods.

(i) When A is a carbonyl group or a sulfonyl group, $R_6$ is a hydrogen atom or a lower alkylsulfonyl group, and $R_7$ is a lower alkyl group, a halogenated lower alkyl group, a mono- or di-lower alkylamino group, a mono- or di-lower alkylaminoalkyl group, or an unsubstituted phenyl group or a phenyl group substituted with a halogen atom, a lower alkyl group, a lower alkoxy group, or a trifluoromethyl group, a primary amino compound expressed by the following formula (XIII)

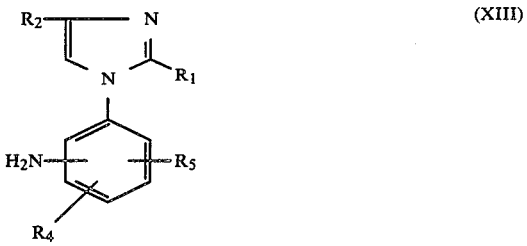

is reacted with a carboxylic acid or sulfonic acid expressed by the following general formula (XIV)

$R_7$-A-OH                            (XIV)

or its reactive derivative (e.g. acid halide, acid anhydride, mixed anhydride or sulfonyl halide) in an inert solvent such as chloroform, dichloromethane, benzene, toluene, xylene or the like which does not take part in the reaction and, if necessary, in the presence of a deoxidizer such as potassium carbonate, sodium carbonate, triethylamine or pyridine at a temperature of 0°–150° C., thereby obtaining the intended compound of the formula (I)

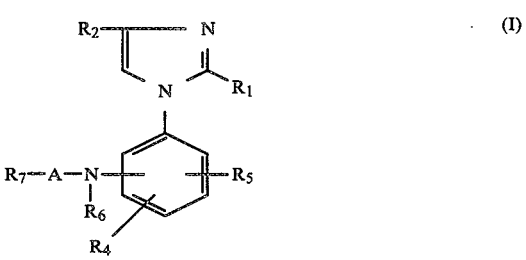

(ii) When A is a carbonyl group, $R_6$ is a hydrogen atom, and $R_7$ is a lower alkylamino group, or an unsubstituted phenylamino group or a phenylamino group substituted with a halogen atom, a lower alkyl group, a lower alkoxy group or a trifluoromethyl group, the compound expressed by the afore-indicated formula (XIII) is reacted with an isocyanate expressed by the formula, $R_8NCO$, (XV) (in which $R_8$ represents a lower alkyl group or an unsubstituted phenyl group or a phenyl group substituted with a halogen atom, a lower alkyl group, a lower alkoxy group, or a trifluoromethyl group) in an inert solvent which does not take part in the reaction, e.g. chloroform, dichloromethane, benzene, toluene, xylene or pyridine at a temperature of room temperature to 100° C., thereby obtaining the intended compound of the general formula (I)

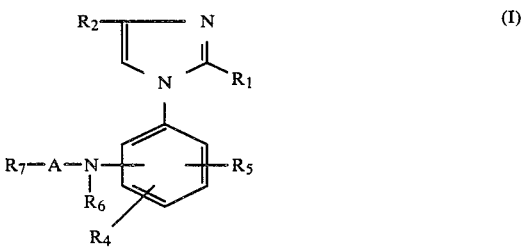

(iii) When A is a carbonyl group or a sulfonyl group, $R_6$ is a lower alkyl group, and $R_7$ is a lower alkyl group, or an unsubstituted phenyl group or a phenyl group substituted with a halogen atom, a lower alkyl group, a lower alkoxy group or a trifluoromethyl group, compounds of the following general formula (I) can be prepared as follows:

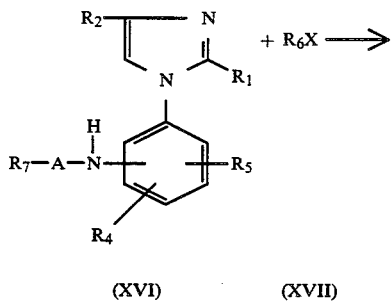

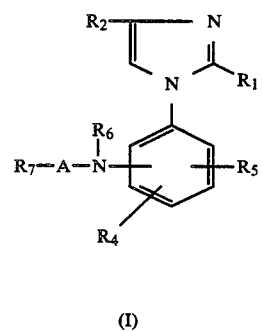

That is, the compound of the general formula (XVI) (wherein $R_1$, $R_2$, $R_4$ and $R_5$ have the same meanings as defined hereinbefore, respectively) is reacted with the compound of the general formula (XVII) (wherein $R_6$ represents a lower alkyl group and X represents a halogen atom) in the presence of an alkali carbonate, an alkali hydride, or an alkoxyalkali in a solvent such as DMF (N,N-dimethylformamide), HMPA (hexamethylphosphoramide), or DMSO (dimethylsulfoxide), thereby obtaining the intended compound of the above formula (I).

From the viewpoint of the chemical structure of the compounds according to the present invention and in view of the conventional knowledge, it cannot be expected at all that the compounds according to the present invention will exert an antidepressant efficacy. The antidepressant efficacy of the compounds according to the present invention are specific and considerably strong.

The antidepressant efficacy of the compounds according to the present invention will now be described.

[Pharmacological Tests]

TEST COMPOUNDS

The following compounds are selected as compounds to be tested from the compounds of the general formula (I) according to the present invention.

1-(3,4-Dimethylphenyl)-2-methylimidazole (hereinafter referred to as "compound A")
1-(4-Dimethylaminophenyl)-2-methylimidazole (hereinafter referred to as "compound B")
1-(3,4-Dichlorophenyl)-2-ethylimidazole (hereinafter referred to as "compound C")
1-(4-Aminophenyl)-2,4-dimethylimidazole (hereinafter referred to as "compound D")
1-(3-Trifluoromethyl-4-aminophenyl)-2-methylimidazole (hereinafter referred to as "compound E")
1-(4-Aminophenyl)-2-ethylimidazole (hereinafter referred to as "compound F")
1-(2-Chloro-4-aminophenyl)-2-methylimidazole (hereinafter referred to as "compound G")
1-(3-Aminophenyl)-2-methylimidazole (hereinafter referred to as "compound H")
1-(3-Amino-4-methylphenyl)-2-methylimidazole (hereinafter referred to as "compound I")
1-(4-n-Butylaminophenyl)-2-methylimidazole (hereinafter referred to as "compound J")
1-(4-Aminophenyl)-2-methylimidazole (hereinafter referred to as "compound K")
1-[4-(4-Chlorobenzoylamino)phenyl]-2-methylimidazole (hereinafter referred to as "compound L")
1-[4-(4-Fluorobenzoylamino)phenyl]-2-methylimidazole (hereinafter referred to as "compound M")
1-[4-(4-Chlorobenzoylamino)phenyl]-2-ethylimidazole (hereinafter referred to as "compound N")
1-[4-(4-Methylbenzoylamino)phenyl]-2-ethylimidazole (hereinafter referred to as "compound O")
1-[4-(4-Chlorobenzoylamino)phenyl]-2-isopropylimidazole (hereinafter referred to as "compound P")
1-[4-(4-Methylbenzoylamino)phenyl]-2-methylimidazole (hereinafter referred to as "compound Q")

Each test compound is used in the form of a hydrochloride.

EXPERIMENTAL PROCEDURES (1) Anti-reserpine activity:

The antagonism against the reserpine-induced hypothermia is examined according to the method of B. M. Askew (Life Science, 4, 725–730, 1963).

Male ddy mice having a body weight of 19 to 25 g are used as the test animal. Reserpine is injected intraperitoneally in dose of 2.5 mg/kg, and 18 hours after the injection, the test compound is orally administered and the change of the body temperature with the lapse of time is examined by using a thermistor type thermometer (Model MGA III manufactured by Shibaura Denshi).

The effect of each compound is examined with 2 to 4 dose levels.

Each of the test compound is used in the form of an aqueous solution. The control animal is treated with physiological saline solution. Four animals having a body temperature of 24° to 25° C., 18 hours after the injection of reserpine, are used for each dose. The experiment is carried out in a room at 23° to 25° C.

(2) Influence on spontaneous motility:

The spontaneous motility is examined according to the method of T. H. Sevensson. (Psychopharmacologia, 14, 157, 1969). Three ddy male mice having a body weight of 20 to 25 g are put in a black observation box of an acrylic resin as one group, and the amount of the spontaneous motility during a period of 60 minutes is measured and recorded by using Animex (manufactured by Farrod Co., Sweden).

Sixty minutes before the start of the measurement of the spontaneous motility, the test compound is orally administered in a dose of 40 mg/kg. The control animal is treated with physiological saline solution. Five groups (15 mice) are used for each dose level.

(3) Acute toxicity:

The test compound is administered in a dose of 100 or 400 mg/kg to mice for examining the lethal action. Five mice are used for each dose level. The lethal ratio is measured 24 hours after oral administration.

EXPERIMENTAL RESULTS

Results of the experiment of the anti-reserpine activity, the influence on the spontaneous motility and the acute toxicity are shown in Table A.

TABLE A

| Test Compound | Anti-Reserpine Activity Minimum Effective Dose (mg/Kg)[a] | Relative Spontaneous Motility (%) to Control | Acute Toxicity (Lethal Ratio %) | |
|---|---|---|---|---|
| | | | 100 mg/Kg | 400 mg/Kg |
| A | 2.5 | 82 ± 6 | 0 | 100 |
| B | 2.5 | 526 ± 24* | 0 | 80 |
| C | 1.25–2.5 | 99 ± 7 | 0 | 20 |
| D | 5.0 | 473 ± 48* | 0 | 60 |
| E | 5.0 | 70 ± 8* | 0 | 0 |
| F | 1.25 | 382 ± 25* | 0 | 60 |
| G | 10 | 254 ± 68* | 0 | 40 |
| H | 2.5 | 83 ± 3 | 0 | 0 |
| I | 5.0 | 58 ± 8* | 0 | 20 |
| J | 5.0 | 543 ± 57* | 0 | 60 |
| K | 1.25 | 350 ± 31*[b] | 40 | 80 |
| L | 10 | 367 ± 30* | 0 | 0 |
| M | 10 | 229 ± 30* | 0 | 0 |
| N | 2.5 | 207 ± 51* | 0 | 0 |
| O | 5.0 | 287 ± 23* | 0 | 20 |
| P | 10 | 92 ± 14 | 0 | 0 |
| Q | 10 | 447 ± 51* | 0 | 40 |

Note
*: Significant increase of the spontaneous motility at $P < 0.05$
[a]The minimum dose necessary for increasing the body temperature of reserpine-treated mice significantly ($P < 0.05$) over the control group 10 mg/Kg P.O.

As will be clear from the table A, the compounds of the invention were found to show a potential anti-reserpine activity and to be very low in toxicity.

Furthermore, we investigated the effect of the compound of the present invention (compound H and I) on the level of dopamine and its metabolites in the mouse brain. As a result it was found that these compounds' reduce dopamine turnover in the brain. This means that the compounds of the invention antagonize against the reserpine-induced depression in a way completely different from the known tricyclic antidepressant.

Thus, the compounds of the present invention show a potential and unique anti-reserpine activity and are high in safety because of their weak toxicity and are thus very excellent as a remedy or prophylactic of the depression or depressive state. In addition, the compounds of the invention are considered to differ chemically and pharmacologically from the existing antidepressant (Imipramine, Amitriptyline and the like). In other words, the compounds of the invention are a medicine of the unique type completely different from known antidepressant.

The compounds according to the present invention are administered in doses of 10 to 1000 mg/day, preferably 30 to 300 mg/day, for the clinical treatment of patients suffering from depression or patients suffering from internal diseases and complaining of the depressive state.

The compounds according to the present invention may be formed into various preparations for administration according to optional methods. Therefore, the present invention includes a pharmaceutical composition comprising at least one compound of the present invention suitable as a medicine for the human body. This pharmaceutical composition may be prepared by using an optional pharmaceutical carrier or excipient and be administered according to a customary method.

It is preferred that the pharmaceutical composition be administered in the form suitable for absorption from digestive canals. A tablet or capsule can be mentioned as the unit form for oral administration, which may comprise binders such as syrup, gum arabic, gelatin, sorbitol, traganth and polyvinyl alcohol, excipients such as lactose, corn starch, calcium phosphate, sorbitol and glycine, lubricants such as magnesium stearate, talc, polyethylene glycol and silica, and disintegrating agents such as potato starch, wetting agents such as sodium lauryl sulfate, and other conventional adjuvants. Tablets may be coated according to known methods customary adopted in the art. Liquid preparations for oral administration include aqueous and oily suspensions and solutions, syrups, elixirs and the like. Furthermore, a dry product which is re-dissolved in water or other appropriate vehicle before administration may be used. These liquid preparations may include additives customarily used in this field, for example, suspending agents such as sorbitol syrup, methyl cellulose, glucose/sugar syrup, gelatin, hydroxyethyl cellulose, carboxymethyl cellulose, aluminum stearate gel and hydrogenated edible oil, emulsifiers such as lecithin, sorbitol mono-oleate and gum arabic, non-aqueous vehicles such as almond oil, fractionated coconut oil, oily ester, propylene glycol and ethyl alcohol, and antiseptic agents such as methyl p-hydroxybenzoate, propyl p-hydroxybenzoate and sorbic acid.

An injection composition is provided in the form of an ampoule or vial containing a unit dosage for administration together with an antiseptic agent. The injection composition may be in the form of a suspension, a solution or an emulsion in an oily or aqueous vehicle, which may contain a suspending agent, a stabilizer and/or a dispersant. The active ingredient may be a powder which is re-dissolved in an appropriate vehicle such as sterilized water free of a pyrogenic substance before administration.

This invention will be illustrated more particularly by the following examples, but this invention is of course not limited only to these examples.

EXAMPLE 1

Synthesis of 1-(3,4-dimethylphenyl)-2-methylimidazole

A mixture of 2.0 g of 2-methyl-oxazole-4-carboxylic acid and 6.0 g of xylidine was heated on an oil bath at an external temperature of 180° C. for 40 minutes under agitation. The reaction product was purified by silica gel column chromatography (using ethyl ether as an eluting solvent) to obtain 2.6 g of the intended compound having a melting point of 84° to 85° C. The product was converted to a hydrochloride having a melting point of 255° C. (decomposition) according to a customary method. Elementary analysis values as $C_{12}H_{14}N_2 \cdot HCl$ were as follows.

Calculated: C=64.9%, H=6.80%, N=12.58%;
Found: C=64.77%, H=6.77%, N=12.52%.

EXAMPLE 2

Synthesis of 1-(3,4-dichlorophenyl)-2-ethylimidazole

A mixture of 1.5 g of 2-ethyl-oxazole-4-carboxylic acid and 5.2 g of 3,4-dichloroaniline was heated on an oil bath at an external temperature of 170° to 180° C. for 40 minutes under agitation. The reaction product was purified by silica gel column chromatography (using a liquid mixture of ethyl ether, benzene and ethanol as an eluting solvent) to obtain 1 g of the intended compound having a melting point of 95° to 96° C. Its hydrochloride had a melting point of 250° C. Elementary analysis values as $C_{11}H_{10}Cl_2N_2.HCl$ were as follows.

Calculated: C=47.57%, H=4.00%, N=10.09%; Found: C=47.48%, H=3.90%, N=10.01%.

EXAMPLE 3

Synthesis of 1-(4-aminophenyl)-2-methylimidazole 13.5 g of 2-methyl-1-(4-nitrophenyl)imidazole was hydrogenated in the presence of 10% Pd/c in 160 ml of ethanol at 30° to 40° C. at an initial pressure of 40 kg/cm². After 3 hours, the reduction mixture was filtered and the solvent was removed from the filtrate under reduced pressure. The residue was recrystallized from a mixed solvent of benzene and n-hexane to obtain 9.8 g of the intended compound having a melting point of 112° to 113° C. Elementary analysis values as $C_{10}H_{11}N_3$ were as follows.

Calculated: C=69.33%, H=6.41%, N=24.26%; Found: C=69.31%, H=6.46%, N=23.96%.

EXAMPLE 4

Synthesis of 1-(3-amino-4-methylphenyl)-2-methylimidazole

(i) Synthesis of 1-(4-methyl-3-nitrophenyl)-2-hydroxymethylimidazole

In a sealed tube, 12 g of 1-(4-methyl-3-nitrophenyl)-imidazole was reacted with 12 ml of 37% formalin at 140° C. for 12 hours, and 6 ml of 37% formalin was further added and reaction was conducted for 9 hours under the same conditions as described above. The reaction mixture was cooled and water was added thereto. The precipitated crystal was recovered by filtration, dried and recrystallized from dimethyl formamide to obtain 10.2 g of the intended compound having a melting point of 185° C. Elementary analysis values as $C_{11}H_{11}N_3O_4$ were as follows.

Calculated: C=56.64%, H=4.76%, N=18.02%; Found: C=56.42%; H=4.69%, N=17.93%.

(ii) Synthesis of 1-(4-methyl-3-nitrophenyl)-2-chloromethylimidazole

To 8 g of 1-(4-methyl-3-nitrophenyl)-2-hydroxymethylimidazole obtained in (i) above was added 25.5 ml of thionyl chloride, and the mixture was refluxed with stirring for 5 hours. The reaction mixture was cooled and diethyl ether was added thereto. The precipitated crystal was recovered by filtration to obtain 9.6 of the intended compound (hydrochloride).

(iii) Synthesis of 1-(3-amino-4-methylphenyl)-2-methylimidazole

A solution of 4.3 g of 1-(4-methyl-3-nitrophenyl)-2-chloromethylimidazole hydrochloride obtained in (ii) above in 40 ml of water and 100 ml of ethanol with 0.4 g of 10% Pd/c was hydrogenated at 50° C. at an initial pressure of 40 kg/cm². After 4 hours, the reaction mixture was filtered and the solvent was removed from the filtrate under reduced pressure. An aqueous solution of sodium carbonate was added to the residue, until the resulting solution had become alkaline. Then, the solution was extracted with chloroform. The chloroform layer was washed with water and dried over MgSO₄, and chloroform was evaporated under reduced pressure. The residue was recrystallized from a mixed solvent of benzene and n-hexane to obtain 2.2 g of the intended compound having a melting point of 126° to 128° C. The so obtained compound was converted to a hydrochloride having a melting point of 234° C. decomposition. Elementary analysis values as $C_{11}H_{13}N_3.2HCl$ were as follows.

Calculated: C=50.76%, H=5.82%, N=16.15%; Found: C=50.59%, H=5.91%, N=15.92%.

EXAMPLE 5

Synthesis of 1-(4-n-butylaminophenyl)-2-methylimidazole

(i) Synthesis of 1-(4-acetoaminophenyl)-2-methylimidazole

A mixture of 6 g of 1-(4-aminophenyl)-2-methylimidazole and 30 ml of acetic anhydride was refluxed with stirring for 3 hours, and the reaction mixture was subjected to distillation under reduced pressure. Water was added to the residue and the precipitated crystal was recovered by filtration and purified by silica gel chromatography using a benzene-alcohol mixed solvent as an eluting solvent to obtain 2.1 g of the intended compound having a melting point of 177° C. Elementary analysis values as $C_{14}H_{19}N_3$ were as follows.

Calculated: C=73.36%, H=8.30%, N=18.34%; Found: C=73.33%, H=8.27%, N=18.29%.

(ii) Synthesis of 1-(4-n-butylaminophenyl)-2-methylimidazole

Under N₂, 1.7 g of 1-(4-acetoaminophenyl)-2-methylimidazole was dissolved in 15 ml of dimethylformamide, and 0.38 g of 55% sodium hydride was added to the solution. The solution was stirred at room temperature for 20 minutes and at 60° to 70° C. for 10 minutes. Then, a solution of 1.5 g of n-butyl iodide in a small quantity of dimethyl formamide was added dropwise to the reaction mixture. Then, the mixture was stirred at 60° to 70° C. for 2 hours. Dimethylformamide was evaporated under reduced pressure, and 20 ml of 10% hydrochloric acid was added to the residue. The mixture was refluxed with stirring for 2 hours, cooled and washed with chloroform. The aqueous layer was, recovered, made alkaline with an aqueous solution of sodium carbonate and extracted with chloroform. The chloroform layer was washed with water and dried over MgSO₄, and chloroform used as the solvent was removed by distillation under reduced pressure. The residue was purified by silica gel chromatography using a benzene-ethanol mixture solvent as an eluting solvent to obtain 0.9 g of the intended compound. The obtained compound was converted to a hydrochloride having a melting point of 189° to 192° C. Elementary analysis values as $C_{14}H_{10}N_3.HCl.1/6H_2O$ were as follows.

Calculated: C=62.54%, H=7.76%, N=15.63%; Found: C=62.42%, H=7.85%, N=15.37%.

EXAMPLE 6

Synthesis of 1-[4-(4-chlorobenzoylamino)phenyl]-2-ethylimidazole 1.9 g of 1-(4-aminophenyl)-2-ethylimidazole was added to a solution of 2.6 g of p-chlorobenzoyl chloride in 50 ml of toluene, and the mixture was refluxed with stirring for 7 hours. The reaction mixture was naturally cooled and diethyl ether was then added thereto. The precipitated crystal was recovered by filtration, washed sufficiently with ethyl ether and recrystallized from ethanol and then from water to obtain 2.5 g of the intended compound in the form of a hydrochloride. The melting point was 265° to 267° C. Elementary analysis values as $C_{18}H_{16}ClN_3O \cdot HCl \cdot 1/2H_2O$ were as follows.

Calculated: C=58.21%, H=4.89%, N=11.32%; Found: C=58.23%, H=4.75%, N=11.06%.

EXAMPLE 7

Synthesis of 1-[2-(N,N-dimethylsulfonylamino)phenyl]-2-methylimidazole

A mixture of 1.1 g of triethylamine and 1.2 g of methanesulfonyl chloride was added to a solution of 1.5 g of 1-(2-aminophenyl)-2-methylimidazole in 30 ml of chloroform, and the mixture was refluxed with stirring for 5 hours. Then, 0.6 g of methanesulfonyl chloride was added to the reaction mixture and the mixture was refluxed with stirring for 3 hours. After completion of the reaction, the reaction mixture was naturally cooled and the solvent was removed by distillation under reduced pressure. Water was added to the residue and the resulting liquid was made alkaline by addition of an aqueous solution of sodium carbonate. The precipitated crystal was recovered by filtration, and washed with water, recrystallized from ethanol to obtain 0.9 g of the intended compound. The obtained compound was converted to a hydrochloride having a melting point of 215° to 220° C. according to customary procedures. Elementary analysis values as $C_{12}H_{15}N_3S_2O_4 \cdot HCl$ were as follows.

Calculated: C=39.40%, H=4.42%, N=11.49%; Found: C=39.21%, H=4.33%, N=11.23%.

EXAMPLE 8

Synthesis of 2-ethyl-1-[4-(N'-methylureido)phenyl]imidazole 0.8 g of methyl isocyanate was added to a solution of 1.5 g of 1-(4-aminophenyl)-2-ethylimidazole in 20 ml of dichloromethane, and the mixture was stirred at room temperature for 3 hours and then refluxed with stirring for 3 hours. After completion of the reaction, the reaction mixture was naturally cooled and the solvent was removed by distillation under reduced pressure. Benzene was added to the residue, and the formed solid was recovered by filtration. The recovered solid was dissolved in a small quantity of methanol and recrystallized from an ethyl ether/benzene mixed solvent. The obtained compound was converted to a hydrochloride having a melting point of 228° to 232° C. according to customary procedures. Elementary analysis values as $C_{13}H_{16}N_4O \cdot HCl$ were as follows.

Calculated: C=55.60%, H=6.11%, N=19.96%; Found: C=55.53%, H=5.86%, N=20.00%.

EXAMPLE 9

Synthesis of 1-(3-amino-4-methylphenyl)-2-methylimidazole

A mixture of 4.5 g of 2-methylimidazole, 6.9 g of 2-amino-4-chlorotoluene, 7.5 g of potassium carbonate and 0.5 g of copper powder was stirred at 200° C. for 5 hours. After cooling, dilute hydrochloric acid was added to the reaction mixture, until the solution had become acidic and then insoluble materials were removed by filtration. The filtrate was again made alkaline by addition of sodium carbonate and extracted with chloroform (50 ml×3), followed by washing with water and drying over $MgSO_4$. Thereafter, chloroform was evaporated under reduced pressure and the resulting residue was purified by a silica gel column chromatography (eluded with a chloroform-methanol system) to obtain 2.1 g of a intented compound (m.p. 126°-8° C.). This compound was converted into its hydrochloride (m.p. 234° C.) by a usual manner.

Elementary Analysis: Calculated (%) for $C_{11}H_{13}N_3 \cdot 2HCl$; C=50.76, H=5.82, N=16.15; Found (%) C=50.56, H=5.85, N=16.85.

Other compounds according to the present invention are described in the following Table as Examples.

TABLE 1

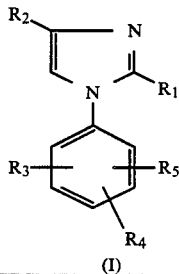

(I)

| Example No. | R₁ | R₂ | $\begin{array}{c}R_3\\ \diagdown\\ \diagup\\ R_5\end{array}$ phenyl with R₄ | Molecular Formula Melting Point (°C.) | | Elementary Analysis Values (%) C | H | N |
|---|---|---|---|---|---|---|---|---|
| 10 | CH₃ | H | 2,3,4-tri-OCH₃-phenyl | C₁₃H₁₆N₂O₃·HCl·3/4H₂O 139–141 | Calculated Found | 52.33 52.23 | 6.20 5.95 | 9.44 9.44 |
| 11 | CH₃ | CH₃ | 4-NH₂-phenyl | C₁₁H₁₃N₃·2HCl 264 | Calculated Found | 50.76 50.54 | 5.82 5.80 | 16.15 16.26 |
| 12 | CH₃ | H | 4-OCH₃-phenyl | C₁₁H₁₂N₂O·HCl 219–222 | Calculated Found | 58.78 58.65 | 5.84 5.60 | 12.47 12.42 |
| 13 | CH₃ | H | 3,4-di-OCH₃-phenyl | C₁₂H₁₄N₂O₂·HCl 245–247 | Calculated Found | 56.57 56.57 | 5.94 5.82 | 11.00 11.00 |
| 14 | CH₃ | H | 2-OCH₃-phenyl | C₁₁H₁₂N₂O·HCl 201–203 | Calculated Found | 58.78 58.54 | 5.84 5.79 | 12.47 12.47 |
| 15 | CH₃ | H | 4-F-phenyl | C₁₀H₉FN₂·HCl 235–238 | Calculated Found | 56.46 56.38 | 4.75 4.73 | 13.17 13.40 |
| 16 | CH₃ | H | 4-piperidino-phenyl | C₁₅H₁₉N₃·2HCl 189–191 | Calculated Found | 57.31 57.26 | 6.75 6.81 | 13.37 13.39 |
| 17 | CH₃ | H | 4-N(CH₃)₂-phenyl | C₁₂H₁₅N₃·2HCl·3/4H₂O 214–216 | Calculated Found | 50.08 49.97 | 5.79 5.97 | 14.60 14.76 |
| 18 | CH₃ | H | 4-Cl-phenyl | C₁₀H₉ClN₂·HCl·1/6H₂O 195–197 | Calculated Found | 51.72 51.99 | 4.49 4.31 | 12.06 12.24 |

TABLE 1-continued

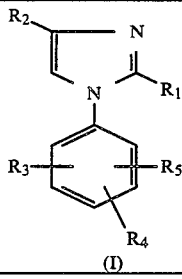

(I)

| Example No. | $R_1$ | $R_2$ | $R_3$ $R_4$ $R_5$ | Molecular Formula Melting Point (°C.) | | Elementary Analysis Values (%) C H N |
|---|---|---|---|---|---|---|
| 19 | $CH_3$ | H | 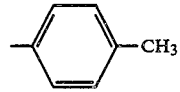 4-$CH_3$ | $C_{11}H_{12}N_2 \cdot HCl$<br>220 | Calculated<br>Found | 63.29  6.29  13.42<br>63.15  6.29  13.42 |
| 20 | $C_2H_5$ | H | 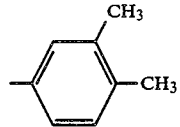 2,3-di-$CH_3$ | $C_{13}H_{16}N_2 \cdot HCl$<br>222 | Calculated<br>Found | 65.93  7.25  11.83<br>65.97  7.06  11.95 |
| 21 | $CH_3$ | H | 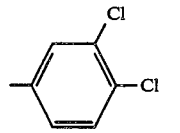 3,4-di-Cl | $C_{10}H_8Cl_2N_2 \cdot HCl$<br>230 | Calculated<br>Found | 45.54  3.45  10.63<br>45.29  3.33  10.56 |
| 22 | n-$C_3H_7$ | H | 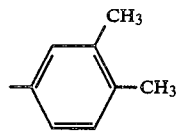 2,3-di-$CH_3$ | $C_{14}H_{18}N_2 \cdot HCl$<br>150–151 | Calculated<br>Found | 67.03  7.65  11.17<br>67.02  7.71  11.16 |
| 23 | $CH_3$ | H | 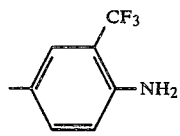 3-$CF_3$, 4-$NH_2$ | $C_{11}H_{10}F_3N_3 \cdot HCl \cdot 1/2H_2O$<br>246–249 | Calculated<br>Found | 46.57  4.16  14.81<br>46.63  3.90  14.96 |
| 24 | $CH_3$ | H | 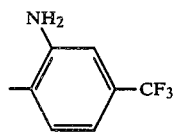 3-$NH_2$, 5-$CF_3$ | $C_{11}H_{10}F_3N_3 \cdot HCl$<br>>246 | Calculated<br>Found | 42.04  3.86  13.38<br>42.00  3.82  13.52 |
| 25 | $C_2H_5$ | H | 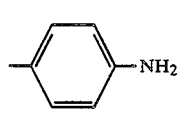 4-$NH_2$ | $C_{11}H_{13}N_3 \cdot 2HCl$<br>255 | Calculated<br>Found | 50.76  5.82  16.15<br>50.57  5.75  16.18 |
| 26 | $C_2H_5$ | H | 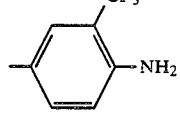 3-$CF_3$, 4-$NH_2$ | $C_{12}H_{12}F_3N_3 \cdot HCl$<br>243–246 | Calculated<br>Found | 49.40  4.50  14.41<br>49.31  4.43  14.36 |
| 27 | 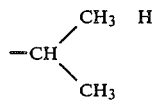 $-CH(CH_3)_2$ | H | 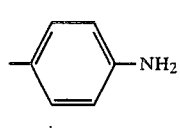 4-$NH_2$ | $C_{12}H_{15}N_3 \cdot 2HCl$<br>>225 | Calculated<br>Found | 52.54  6.26  15.32<br>52.33  6.36  15.15 |

TABLE 1-continued

Structure (I):

$R_2$ at position on imidazole ring; $R_1$ attached; N-phenyl substituted with $R_3$, $R_4$, $R_5$.

| Example No. | $R_1$ | $R_2$ | $R_3$, $R_4$, $R_5$ (phenyl substituent) | Molecular Formula Melting Point (°C.) | | Elementary Analysis Values (%) C | H | N |
|---|---|---|---|---|---|---|---|---|
| 28 | CH$_3$ | H | 3-Cl, 4-NH$_2$ phenyl | C$_{10}$H$_{10}$N$_3$Cl.2HCl<br>181–185 | Calculated<br>Found | 42.78<br>42.43 | 4.32<br>4.61 | 14.99<br>14.59 |
| 29 | CH$_3$ | H | 3-NH$_2$ phenyl | C$_{10}$H$_{11}$N$_3$.2HCl<br>228–231 | Calculated<br>Found | 48.77<br>48.72 | 5.33<br>5.41 | 17.07<br>17.06 |
| 30 | —C$_3$H$_7$ | H | 4-NH$_2$ phenyl | C$_{12}$H$_{15}$N$_3$.2HCl<br>209–212 | Calculated<br>Found | 52.54<br>52.25 | 6.26<br>6.15 | 15.32<br>15.11 |
| 31 | —CH$_3$ | H | 4-NHSO$_2$CH$_3$ phenyl | C$_{11}$H$_{13}$N$_3$SO$_2$.HCl<br>254–256 | Calculated<br>Found | 45.91<br>45.66 | 4.91<br>4.85 | 14.61<br>14.46 |
| 32 | —C$_2$H$_5$ | H | 4-NHCO-(4-CH$_3$-phenyl) phenyl | C$_{19}$H$_{19}$N$_3$O.HCl<br>234 | Calculated<br>Found | 66.74<br>66.53 | 5.91<br>5.96 | 12.23<br>12.35 |
| 33 | —C$_2$H$_5$ | H | 4-NHSO$_2$-(4-Cl-phenyl) phenyl | C$_{17}$H$_{16}$ClN$_3$O$_2$S.HCl<br>236–240 | Calculated<br>Found | 51.24<br>51.42 | 4.31<br>4.20 | 10.55<br>10.25 |
| 34 | —CH$_3$ | H | 4-NHCONH-(4-Cl-phenyl) phenyl | C$_{17}$H$_{15}$ClN$_4$O.HCl.1/6H$_2$O<br>246–249 | Calculated<br>Found | 55.73<br>55.74 | 4.50<br>4.46 | 15.30<br>15.02 |
| 35 | —CH$_3$ | H | 4-NHCO-(4-Cl-phenyl) phenyl | C$_{17}$H$_{14}$ClN$_3$O<br>195–197 | Calculated<br>Found | 65.47<br>65.37 | 4.53<br>4.82 | 13.48<br>13.27 |
| 36 | —CH$_3$ | H | NHCO-(2-Cl-phenyl) phenyl | C$_{17}$H$_{14}$ClN$_3$O<br>240–242 | Calculated<br>Found | 65.47<br>65.34 | 4.53<br>4.61 | 13.48<br>13.37 |

TABLE 1-continued

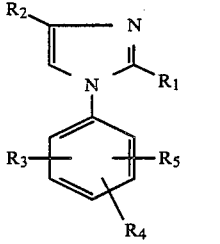
(I)

| Example No. | $R_1$ | $R_2$ | $R_3$, $R_4$, $R_5$ (aryl substituent) | Molecular Formula Melting Point (°C.) | | Elementary Analysis Values (%) C | H | N |
|---|---|---|---|---|---|---|---|---|
| 37 | —CH$_3$ | H | 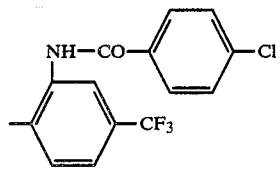 | C$_{18}$H$_{13}$F$_3$ClN$_3$O.HCl 185–190 | Calculated Found | 51.92 51.62 | 3.40 3.42 | 10.10 10.01 |
| 38 | —CH$_3$ | H | 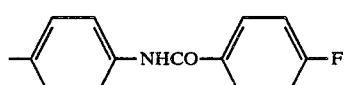 | C$_{17}$H$_{14}$FN$_3$O.HCl.1/6H$_2$O 270 | Calculated Found | 60.98 61.02 | 4.62 4.61 | 12.55 12.78 |
| 39 | —CH$_3$ | —CH$_3$ | 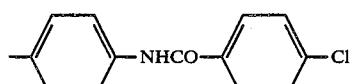 | C$_{18}$H$_{16}$ClN$_3$O.HCl 260–264 | Calculated Found | 59.66 59.61 | 4.74 5.10 | 11.66 11.66 |
| 40 | —C$_2$H$_5$ | H | 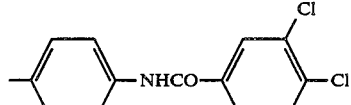 | C$_{18}$H$_{15}$Cl$_2$N$_3$O.HCl 216–218 | Calculated Found | 54.47 54.13 | 4.07 3.83 | 10.59 10.41 |
| 41 | —C$_2$H$_5$ | H | 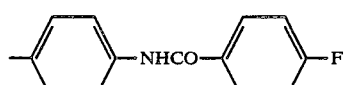 | C$_{18}$H$_{16}$FN$_3$O.HCl.2/3H$_2$O 235 | Calculated Found | 60.41 60.52 | 5.17 4.97 | 11.74 11.67 |
| 42 | —CH$_3$ | H | 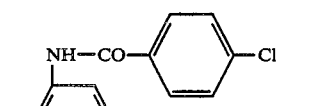 | C$_{17}$H$_{14}$ClN$_3$O 127–129 | Calculated Found | 65.47 65.21 | 4.53 4.39 | 13.48 13.37 |
| 43 | —CH(CH$_3$)$_2$ | H | 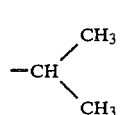 | C$_{19}$H$_{18}$N$_3$ClO.HCl.1/3H$_2$O 258–261 | Calculated Found | 59.67 59.71 | 5.20 5.21 | 10.99 10.96 |
| 44 | —C$_2$H$_5$ | H | 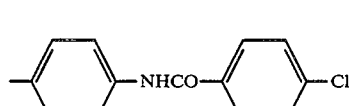 | C$_{19}$H$_{19}$N$_3$O$_2$.HCl 231–234 | Calculated Found | 63.76 63.42 | 5.64 5.60 | 11.74 11.51 |
| 45 | —CH$_3$ | H | 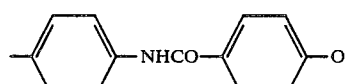 | C$_{18}$H$_{17}$N$_3$O.HCl 266 | Calculated Found | 65.93 66.04 | 5.54 5.62 | 12.82 12.89 |

TABLE 1-continued

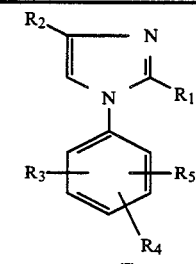

(I)

| Example No. | R₁ | R₂ | Ar (R₃,R₄,R₅ substituted phenyl) | Molecular Formula Melting Point (°C.) | | Elementary Analysis Values (%) C | H | N |
|---|---|---|---|---|---|---|---|---|
| 46 | —C₃H₇ | H | 4-(4-chlorobenzamido)phenyl: —C₆H₄—NHCO—C₆H₄—Cl | C₁₉H₁₈ClN₃O·HCl 230 | Calculated Found | 60.62 60.77 | 5.10 5.11 | 11.17 11.12 |
| 47 | —CH₃ | H | 4-[N-methyl-(4-chlorobenzamido)]phenyl: —C₆H₄—N(CH₃)—CO—C₆H₄—Cl | C₁₉H₁₈N₃ClO·1/2H₂O 133–135 | Calculated Found | 65.40 65.18 | 5.50 5.25 | 12.05 12.08 |
| 48 | —CH₃ | H | 4-acetamidophenyl: —C₆H₄—NH—COCH₃ | C₁₄H₁₉N₃ 177 | Calculated Found | 73.36 73.33 | 8.30 8.27 | 18.34 18.29 |
| 49 | —C₂H₅ | H | 4-(3-trifluoromethylbenzamido)phenyl: —C₆H₄—NH—CO—C₆H₄—CF₃ | C₁₉H₁₆F₃N₃O·HCl 183–184 | Calculated Found | 57.64 57.51 | 4.34 4.52 | 10.62 10.50 |
| 50 | —C₂H₅ | H | 4-aminophenyl: —C₆H₄—NH₂ | C₁₁H₁₃N₃·2HCl 240 (Dec.) | Calculated Found | 50.76 50.56 | 5.82 5.52 | 16.16 16.46 |
| 51 | —CH₃ | H | 2-methoxy-3-aminophenyl (—OCH₃, —NH₂) | C₁₁H₁₃N₃O·2HCl·1/2H₂O 207–9 | Calculated Found | 46.32 46.10 | 5.66 5.48 | 14.73 14.37 |
| 52 | —CH₃ | H | 4-dimethylaminophenyl: —C₆H₄—N(CH₃)₂ | C₁₂H₁₅N₃·2HCl 198–200 | Calculated Found | 52.54 52.41 | 6.26 6.62 | 15.32 15.19 |
| 53 | —CH₃ | H | 4-methylaminophenyl: —C₆H₄—NHCH₃ | C₁₁H₁₃N₃·2HCl 230–3° | Calculated Found | 50.76 50.43 | 5.82 6.13 | 16.15 15.88 |
| 54 | —C₂H₅ | H | 4-propionamidophenyl: —C₆H₄—NHCOC₂H₅ | C₁₄H₁₇N₃O·HCl 278° (Dec.) | Calculated Found | 60.08 60.08 | 6.50 6.39 | 15.02 14.93 |

TABLE 1-continued

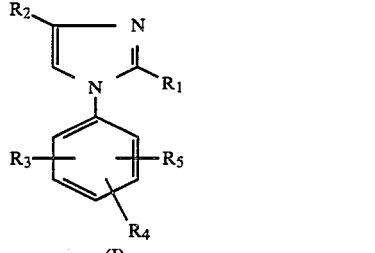

| Example No. | $R_1$ | $R_2$ | $R_3$ $R_4$ $R_5$ | Molecular Formula Melting Point (°C.) | | Elementary Analysis Values (%) C H N |
|---|---|---|---|---|---|---|
| 55 | —CH$_3$ | H | 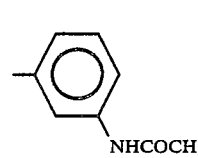 | C$_{12}$H$_{13}$N$_3$O.HCl 236–8° | Calculated Found | 57.24 5.62 16.69<br>57.29 5.76 16.88 |
| 56 | —CH$_3$ | H | 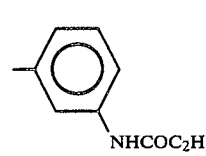 | C$_{13}$H$_{15}$N$_3$O 181–2° | Calculated Found | 68.09 6.61 18.33<br>67.77 6.62 18.14 |
| 57 | —CH$_3$ | H | 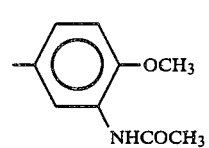 | C$_{13}$H$_{15}$N$_3$O$_2$HCl.H$_2$O 199–201 | Calculated Found | 52.08 6.06 14.02<br>52.21 6.00 14.55 |
| 58 | —CH$_3$ | H | 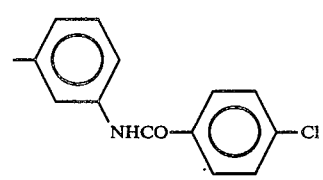 | C$_{17}$H$_{14}$N$_3$OCl.HCl 247.5–249.5 | Calculated Found | 58.61 4.35 12.07<br>58.83 4.33 12.16 |
| 59 | —CH$_3$ | H | 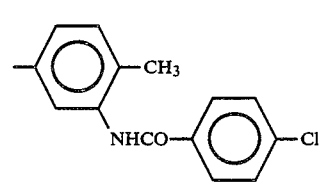 | C$_{18}$H$_{16}$N$_3$ClO.HCl 261–4 | Calculated Found | 59.66 4.74 11.60<br>59.38 4.99 11.34 |

The following are preparation examples according to this invention.

| Preparation example 1 (Capsules) | |
|---|---|
| 1-[4-(4-Chlorobenzoylamino)phenyl]-2-ethylimidazole.hydrochloride | 10 g |
| Corn starch | 90 g |
| Total | 100 g |

A mixture having the above composition was sufficiently blended and filled in hard capsules of gelatin, each capsule containing 100 mg of the mixture. Each capsule contained 10 mg of the main ingredient.

| Preparation example 2 (Tablets) | |
|---|---|
| 1-[4-(4-Chlorobenzoylamino)phenyl]-2-ethylimidazole.hydrochloride | 10 g |
| Crystalline cellulose | 100 g |
| Corn starch | 88 g |
| Calcium stearate | 2 g |
| Total | 200 g |

A mixture having the above composition was sufficiently blended and formed into 1000 flat tablets, each containing 10 mg of the main ingredient.

Preparation example 3 (Tablets)

| | |
|---|---|
| 1-(3',4'-Dichlorophenyl)-2-ethylimidazole. hydrochloride | 10 g |
| Crystalline cellulose | 100 g |
| Corn starch | 88 g |
| Calcium stearate | 2 g |
| Total | 200 g |

A mixture having the above composition was sufficiently blended and formed into 1000 flat tablets, each containing 10 mg of the main ingredient.

Preparation example 4 (Injection)

| | |
|---|---|
| 1-(3',4'-Dichlorophenyl)-2-ethylimidazole. hydrochloride | 10 g |
| Sorbitol | 20 g |
| Physiological saline solution | balance |
| Total | 1 liter |

An injection was prepared from the above composition according to customary procedures. A buffering agent, a pH adjusting agent and an analgesic agent could be added to the above injection according to need.

What we claim is:

1. An imidazole compound of the formula:

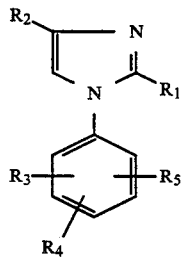

wherein $R_1$ represents a lower alkyl group, $R_2$ represents a hydrogen atom or a lower alkyl group, and $R_3$, $R_4$ and $R_5$ may be the same or different and independently represent a hydrogen atom, a lower alkyl group, a trifluoromethyl group, an amino group, a mono- or a di-lower alkylamino group, or a halogen atom, with the proviso that at least one of $R_3$, $R_4$ and $R_5$ is a trifluoromethyl group, an amino group, a mono- or di-lower alkylamino group, or a halogen atom, or a pharmaceutically acceptable acid addition salt thereof.

2. A compound as claimed in claim 1, wherein $R_2$ is hydrogen or methyl.

3. A compound as claimed in claim 2, wherein $R_3$ is hydrogen.

4. A compound as claimed in claim 3, wherein $R_1$ is methyl or ethyl.

5. A compound as claimed in claim 4, wherein at least one of $R_4$ and $R_5$ is substituted at the 3- or 4-position on the phenyl group of said compound.

6. A compound as defined in claim 1 which is 1-(4-dimethylaminophenyl)-2-methylimidazole; or a pharmaceutically acceptable acid addition salt thereof.

7. A compound as defined in claim 1 which is 1-(3,4-dichlorophenyl)-2-ethylimidazole; or a pharmaceutically acceptable acid addition salt thereof.

8. A compound as defined in claim 1 which is 1-(4-aminophenyl)-2,4-dimethylimidazole; or a pharmaceutically acceptable acid addition salt thereof.

9. A compound as defined in claim 1 which is 1-(3-trifluoromethyl-4-aminophenyl)-2-methylimidazole; or a pharmaceutically acceptable acid addition salt thereof.

10. A compound as defined in claim 1 which is 1-(2-chloro-4-aminophenyl)-2-methylimidazole; or a pharmaceutically acceptable acid addition salt thereof.

11. A compound as defined in claim 1 which is 1-(3-aminophenyl)-2-methylimidazole; or a pharmaceutically acceptable acid addition salt thereof.

12. A compound as defined in claim 1 which is 1-(3-amino-4-methylphenyl)-2-methylimidazole; or a pharmaceutically acceptable acid addition salt thereof.

13. A compound as defined in claim 1 which is 1-(4-n-butylaminophenyl)-2-methylimidazole; or a pharmaceutically acceptable acid addition salt thereof.

14. A compound as defined in claim 1 which is 1-(4-aminophenyl)-2-methylimidazole; or a pharmaceutically acceptable acid addition salt thereof.

15. A pharmaceutical composition for treating depression and depressive states comprising a therapeutically effective amount of a compound as claimed in claim 1, and a pharmaceutical carrier.

16. A method of treating depression and depressive states, which comprises administering to a subject a therapeutically effective amount of a pharmaceutical composition which comprises an imidazole compound of the formula:

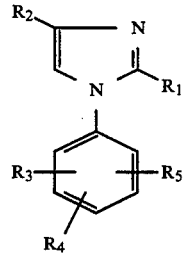

wherein $R_1$ represents a lower alkyl group, $R_2$ represents a hydrogen atom or a lower alkyl group, and $R_3$, $R_4$ and $R_5$ may be the same or different and independently represent a hydrogen atom, a lower alkyl group, a trifluoromethyl group, an amino group, a mono- or di-lower alkylamino group, or a halogen atom, with the proviso that at least one of $R_3$, $R_4$ and $R_5$ is a trifluoromethyl group, an amino group, a mono- or di-lower alkylamino group, or a halogen atom; or a pharmaceutically acceptable acid addition salt thereof, in combination with a pharmaceutical carrier.

17. A method as claimed in claim 16, wherein $R_1$ is methyl or ethyl, $R_2$ is hydrogen or methyl, and $R_3$ is hydrogen.

18. A method as claimed in claim 17, wherein at least one of $R_4$ and $R_5$ is substituted at the 3- or 4-position on the phenyl group of said compound.

19. A method as claimed in claim 16, wherein said compound is administered in a dosage of from 10 to 1000 mg/day.

* * * * *